United States Patent [19]

Hibino et al.

[11] Patent Number: 4,963,494

[45] Date of Patent: Oct. 16, 1990

[54] ENZYME IMMOBILIZATION IN AN ANISOTROPIC ULTRAFILTRATION MEMBRANE

[75] Inventors: Ken Hibino; Takeshi Okada; Kazuo Nakao; Yuko Sahashi, all of Osaka, Japan

[73] Assignee: Nitto Electric Industrial Co., Ltd., Osaka, Japan

[21] Appl. No.: 319,857

[22] Filed: Mar. 6, 1989

Related U.S. Application Data

[63] Continuation of Ser. No. 917,114, Oct. 8, 1986, abandoned.

[30] Foreign Application Priority Data

Oct. 8, 1985 [JP] Japan .................... 60-225435

[51] Int. Cl.$^5$ .................. C12M 1/40; C12N 11/08; C12N 11/06; C12N 11/04
[52] U.S. Cl. .................. 435/288; 435/180; 435/181; 435/182
[58] Field of Search ............. 435/174, 176, 177, 180, 435/181, 182, 288

[56] References Cited

U.S. PATENT DOCUMENTS

| | | | |
|---|---|---|---|
| 4,141,857 | 2/1979 | Levy et al. ............ | 435/180 X |
| 4,266,026 | 5/1981 | Breslau ............ | 435/182 X |
| 4,268,423 | 5/1981 | Rohrbach et al. ............ | 435/176 X |
| 4,440,853 | 4/1984 | Michaels et al. ............ | 435/182 X |

FOREIGN PATENT DOCUMENTS 0069869 1/1983 European Pat. Off. .
1560691 2/1980 United Kingdom .

*Primary Examiner*—David M. Naff
*Attorney, Agent, or Firm*—Sughrue, Mion, Zinn, Macpeak & Seas

[57] ABSTRACT

An enzyme immobilized membrane comprising an anisotropic ultrafiltration membrane having a porous layer and a dense layer, and an enzyme immobilized therein is disclosed. The porous layer of the ultrafiltration membrane retains a water-soluble polymer having at least two functional groups in the crosslinked state, and the enzyme is covalently bonded to the membrane through the functional groups of the polymer. Preferably, the membrane is prepared from polysulfone. The enzyme immobilized membrane is produced by a process which comprises impregnating a solution of the water-soluble polymer into the porous layer of the ultrafiltration membrane under a pressure of 0.1 to 1.0 kg/cm$^2$, washing the porous layer, passing a solution of a crosslinking agent through the porous layer under a pressure within the same pressure range as above to crosslink the water-soluble polymer, removing the non-crosslinked water-soluble polymer by back washing from the dense layer of the membrane, and then passing a solution of the enzyme under a pressure within the same pressure range as above through the porous layer, whereby the enzyme is covalently bonded to the membrane through the functional groups of the polymer.

4 Claims, 1 Drawing Sheet

ENZYME IMMOBILIZATION IN AN ANISOTROPIC ULTRAFILTRATION MEMBRANE

This is a continuation of application Ser. No. 06/917,114 filed 10/8/86, now abandoned.

FIELD OF THE INVENTION

This invention relates to an enzyme immobilized membrane and a process for producing the same.

BACKGROUND OF THE INVENTION

In recent years, enzyme reactions have been actively utilized on a commercial scale in the phamaceutical and food industries. Since enzymes are expensive and when used in the form of a solution, are difficult to separate or recover from the product after reaction, techniques of immobilizing an enzyme on a support material to provide a so-called immobilized enzyme have been extensively studied.

Investigations have been made on the utilization of a membrane such as an ultrafiltration membrane in order to provide a method which enables the separation of the reaction product from the enzyme to be effected simultaneously with the enzyme reaction. Such a method has attracted attention because it makes possible very easily to conduct coarse separation treatment by molecular weight cut-off as a pretreatment of fine separation and purification.

One typical example proposed so far is a membrane reactor on which an enzyme is immobilized. Specifically, a method which comprises enclosing an enzyme into a porous portion of an anisotropic ultrafiltration membrane and coating the porous portion (Japanese Patent Application (OPI) No. 25686/84), and a method which comprises enclosing and entrapping an enzyme together with a gel in the porous portion (Japanese Patent Publication No. 41238/82) are disclosed. None of these methods, however, can retain the enzyme stably. Thus, no membrane has been developed on which an enzyme can be retained and immobilized stably.

SUMMARY OF THE INVENTION

As a result of extensive investigations to achieve the desired enzyme immobilized membrane and a process for producing the same, it has been found that an enzyme immobilized membrane having very high enzyme activity in which the immobilized enzyme has an excellent degree of freeness can be obtained by passing and impregnating a specific water-soluble polymer through and into a porous layer of an anisotropic ultrafiltration membrane under pressures, crosslinking the polymer with a crosslinking agent, and then passing and impregnating a solution of an enzyme through and into the porous layer.

Accordingly, one object of the present invention is to provide an enzyme immobilized membrane which has a high enzyme loading with high activity and an excellent function of separating the product of reaction with a substrate, particularly a low molecular weight product of reaction with a polymeric substrate.

Another object of the present invention is to provide a process for producing the enzyme immobilized membrane with good efficiency.

The enzyme immobilized membrane according to the present invention comprises an anisotropic ultrafiltration membrane having a porous layer and a dense layer, and an enzyme, the porous layer of the ultrafiltration membrane having a water-soluble polymer with at least two functional groups retained therein in the cross-linked state, and the enzyme being covalently bonded to the membrane through the functional groups of the polymer.

The process for producing the enzyme immobilized membrane comprising an anisotropic ultrafiltration membrane having a porous layer and a dense layer and an enzyme immobilized therein according to the present invention comprises impregnating a solution of a water-soluble polymer having at least two functional groups into the porous layer of the membrane under a pressure of 0.1 to 1.0 $kg/cm^2$, washing the porous layer with water, passing a solution of a crosslinking agent through the porous layer under a pressure within the pressure range to crosslink the water-soluble polymer, removing the non-crosslinked portion of the water-soluble polymer by back washing with water from the dense layer of the membrane, and then passing a solution of an enzyme under the pressure range through the porous layer to covalently bond the enzyme to the membrane through the functional groups of the polymer.

BRIEF DESCRIPTION OF THE ACCOMPANYING DRAWINGS

FIG. 1 is a graphic representation showing the results of measurement of the activity of the enzyme immobilized membrane obtained in Example 1; and FIG. 2 is a graphic representation showing the results of measurement of the activity of the enzyme immobilized membrane obtained in Comparative Example 1.

DETAILED DESCRIPTION OF THE INVENTION

Figure 1:
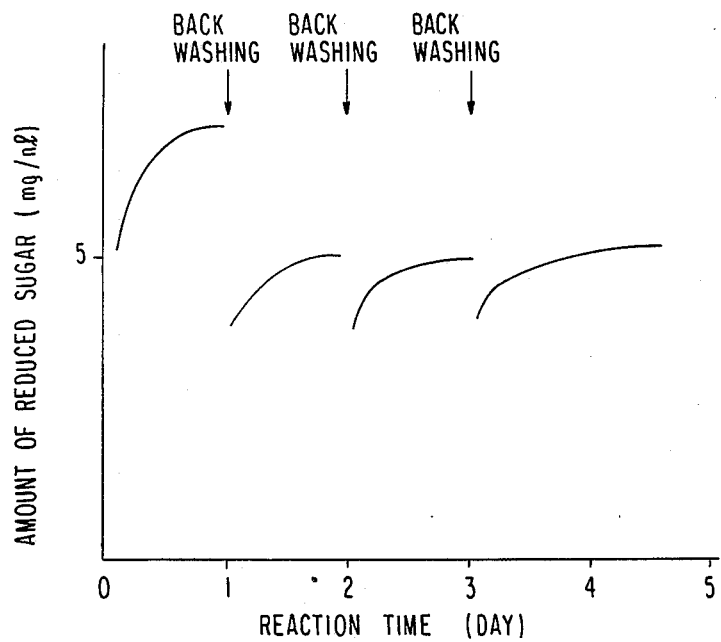

The anisotropic ultrafiltration membrane used in the present invention comprises a dense layer having a molecular weight cut-off of from 1,000 to 1,000,000 and a porous layer having a pore diameter of several micrometers to 100 micrometers supporting the dense layer, and can be of any desired shape such as a flat plate, a tube or a hollow fiber. The form of a hollow fiber membrane is preferred in order to increase its effective membrane area and the contact area of the immobilized enzyme with a substrate.

The ultrafiltration membrane can be prepared from, for example, polysulfone, polyethersulfone, polyamides, polyimides, cellulose acetate and polyacrylonitrile. It is not particularly necessary for these materials to have functional groups capable of reacting with water-soluble polymers or enzymes described hereinbelow, and they should only be film-forming to provide anisotropic ultrafiltration membranes. Of these materials for the membrane, polysulfone, polyamides and polyimides are preferably used because they satisfy the rigorous requirements for molecular weight cut-off required in the production of foods and medicines. The polysulfone is particularly preferred from the standpoint of heat resistance and mechanical strength.

The anisotropic ultrafiltration membrane can be produced by methods known per se. For example, the membrane material described above is dissolved in at least one water-miscible polar organic solvent and then brought into contact with a coagulating liquid composed mainly of water to form an anisotropic ultrafiltration membrane of various shapes having a dense layer on the interface of contact. Examples of the polar organic solvent include dimethyl sulfoxide, dimethylformamide, dimethylacetamide, phenol, cresol, ethylene chlorohydrin, ethylene glycol, propylene glycol, cellosolve, glycerol, methanol, ethanol, propanol, butanol, acetone, dioxane, and tetrahydrofuran. The technique of this invention can be applied to any anisotropic ultrafiltration membranes having a dense layer and a porous layer irrespective of the method of production or their shape.

In producing the enzyme immobilized membrane of the present invention, a water-soluble polymeric material having at least two functional groups is impregnated under pressure in the porous layer of the anisotropic ultrafiltration membrane obtained as above, and the polymeric material is crosslinked with a crosslinking agent. Examples of the water-soluble polymeric material are polyalkyleneimines such as polyethyleneimine, polypropyleneimine and polybutyleneimine; polyalkylene glycols such as polyethylene glycol and polypropylene glycol; polyamino acids such as polylysine and polyarginine; and polyallylamines. Materials having a weight average molecular weight of from about 1,000 to about 200,000 and several tens to several hundred functional groups are preferred. The water-soluble polymeric material can be selected properly depending upon the type of the enzyme used, the type of the material for the membrane, and the shape of the membrane. Of these water-soluble polymers, polyethyleneimine and polyallylamines are preferred because the number of their functional groups can be easily adjusted and their reactivity is high.

In impregnating the solution of the water-soluble polymer in the porous layer of the anisotropic ultrafiltration membrane, the solute concentration of the solution is adjusted to 1% by weight or less, preferably from 0.05 to 0.25 % by weight. If the solute concentration exceeds 1 % by weight, the viscosity of the solution becomes high, and the impregnated water-soluble polymer might clog the pores of the membrane. Consequently, the flux of a substrate solution is decreased to reduce the ultrafilteration performance of the membrane.

As the pressure conditions at the time of impregnating the solution of the water-soluble polymer, the pressure difference between the porous layer and the dense layer of the ultrafiltration membrane is preferably from 0.1 to 1 kg/cm$^2$, and more preferably 0.1 to 0.5 kg/cm$^2$. If the impregnation is carried out under high pressures, the water-soluble polymer is likely to undergo compaction in the inside of the porous layer, particularly on the dense layer side and to clog the pores of the membrane. On the other hand, if the pressure is too low, the impregnation of the water-soluble polymer in the porous layer becomes time-consuming, or the polymer is difficult to impregnate uniformly in the entire porous layer. This is likely to result in impregnation in the surface layer portion only, and in reduction in the amount of the enzyme bonded.

After impregnation, the water-soluble polymer is held by the porous layer of the anisotropic ultrafiltration membrane. The membrane is washed several times to remove impurities and the water-soluble polymer having a very low molecular weight. Thereafter, a solution of a crosslinking agent is passed through the porous layer under the pressure conditions used at the time of impregnating the solution of the water-soluble polymer, usually under the same conditions of impregnation, thereby to crosslink the water-soluble polymer. By applying this crosslinking means, the water-soluble polymer becomes three-dimensionally crosslinked and insolubilized, and the bulkiness and steric hindrance of the molecules increase. Hence, without being bonded to the ultrafiltration membrane itself, the polymer can be retained within the pores of the porous layer and does not flow away by subsequent back washing.

Examples of the crosslinking agent used include dialdehydes such as glyoxal, glutaraldehyde, adipinaldehyde, malondialdehyde and dialdehyde starch; diisocyanates such as hexamethylene diisocyanate and toluene diisocyanate; and diisothiocyanates such as hexamethylenediisothiocyanate. When a polyamino acid is used as the water-soluble polymer, a condensation agent such as water-soluble carbodiimide can be used. Of these, the dialdehydes and diisocyanates can be preferably used because of their relatively high stability and reactivity in aqueous solution.

The crosslinking agent is used in the form of solution. By adjusting the ratio of the molar concentration of the functional groups in the water-soluble polymer to that of the functional groups in the crosslinking agent to from 2 to 50, preferably from 6 to 20, the functional groups to be subsequently bonded to the enzyme can be retained in sufficient amounts. The enzyme can be bonded by utilizing some of the functional groups of the crosslinking agent used. In this case, the crosslinking agent is desirably used in an amount of 1.5 to 20 times the above-described amount.

After the water-soluble polymer is impregnated in the porous layer of the anisotropic ultrafiltration membrane and then crosslinked, the non-crosslinked water-soluble polymer remaining in the porous layer is removed by back washing, which is conventional washing treatment, from the dense layer. Thereafter, a solution of an enzyme is passed from the porous layer and the enzyme is covalently bonded to the membrane through the functional groups of the water-soluble polymer.

Since the water-soluble polymer has functional groups such as an amino group, a carboxyl group and a hydroxyl group in the molecular ends or side chains, these functional groups may be covalently bonded to the functional groups of the enzyme either directly or indirectly through the crosslinking agent or a coupling agent. To increase the mobility of the immobilized enzyme and promotes the enzyme reaction, spacers can be arranged between the water-soluble polymer and the enzyme.

There is no particular limitation on the enzyme used in the present invention. In order to cause the enzyme immobilized membrane of this invention to exhibit fully the characteristics of the ultrafiltration membrane used, it is useful to use the enzyme for hydrolyzing polysaccharides or proteins. Examples of the enzyme which can be used in the present invention are polysaccharide hydrolyzing enzymes such as $\alpha$-amylase, glucoamylase, pectinase, cellulase and muramidase, and protein hydrolyzing enzymes such as papain, pepsin, trypsin, chymotripsin, bromelain and protease. These enzymes produce low molecular weight materials from high molecular weight materials.

The pressure condition employed at the time of passing a solution of the enzyme is adjusted to a range of from 0.1 to 1 kg/cm$^2$ which is the range of the pressure condition used in impregnating the water-soluble polymer or the crosslinking agent, and should not exceed the pressure condition used in the above impregnation. If the degree of pressure is too high, the water-soluble polymer already held is compacted and forms a new layer. This layer impedes the permeation movement of a substrate in an enzyme reaction by passing a solution of the substrate, and the immobilized enzyme cannot be effectively utilized in the reaction.

As described hereinabove, in the enzyme immobilized membrane of the present invention, the crosslinked water-soluble polymer is held in the porous layer of the anisotropic ultrafiltration membrane, and the enzyme is immobilized by being covalently bonded to the functional groups of the polymer. Hence, the enzyme has a degree of freeness which leads to high activity, and in an enzyme reaction, can be used over a long period of time without detachment. According to the process of the present invention, the solution of the water-soluble polymer and the crosslinking agent are impregnated and passed under pressures, and therefore the enzyme immobilized membrane can be produced within a short period of time. Since the membrane retains the enzymes within the membrane pores which are passages of a substrate solution, the contacting of the substrate with the enzyme surely increases, and a large amount of the substrate solution can be treated and separated within short periods of time.

The present invention is described in greater detail by reference to the following examples, but is not to be construed as limited to these examples.

EXAMPLE 1

A small-sized module ($2\phi \times 20$ cm, 200 fibers, membrane area about 800 cm$^2$) of polysulfone hollow fiber membrane for ultrafiltration ("NTU-3050", made by Nitto Electric Industrial Co., Ltd.) was used. A 0.1 % by weight aqueous solution of polyethyeneimine (weight average molecular weight 70,000; about 400 amino groups per molecule) was passed from the porous layer under a pressure of 0.3 kg/cm$^2$ for about 30 minutes.

The porous layer was washed under the same pressure with a large amount of water. While the entire module was maintained at 40° C., a 0.5 % by weight glutaraldehyde solution (phosphate buffer pH 7.0) as a crosslinking agent was passed under the same pressure to crosslink the polyethyleneimine held in the porous layer.

The porous layer was back-washed with water at room temperature to remove the polyethyleneimine which was not held by the porous layer. A 2.5 % by weight glutaraldehyde solution (phosphate buffer pH 7.0) was passed from the porous layer at 40° C. under a pressure of 0.1 kg/cm$^2$ to activate the amino groups of the polyethyleneimine. The module was washed with water under the same pressure, and an alpha-amylase solution ("KOKULASE", a product of Sankyo Corporation; acetate buffer pH 6.0) having a concentration of 2.5 mg/ml was passed through the porous layer under the same pressure to immobilize the enzyme by covalent bonds to give an enzyme immobilized membrane in accordance with the present invention.

COMPARATIVE EXAMPLE 1

An enzyme immobilized membrane was produced by operating in the same way as in Example 1 except that the glutaraldehyde solution as a crosslinking agent was not passed and the polyethylneneimine was not crosslinked.

Figure 2:
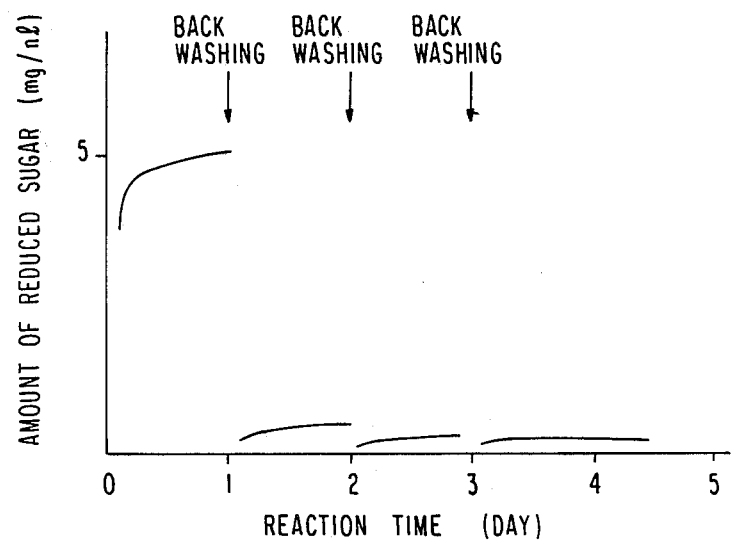

A 1 % by weight soluble starch solution (acetate buffer pH 6.0) was fed into each of the enzyme immobilized membranes obtained in Example 1 and Comparative Example 1 under a pressure of 0.5 kg/cm$^2$, and while the membrane was back-washed from the dense layer at regular intervals, the enzyme reaction was continued at 40° C. The amount of reduced sugar in the permeated solution was measured. The results obtained by using the enzyme immobilized membrane of Example 1 are shown in FIG. 1, and the results obtained by using the enzyme immobilized membrane in Comparative Example 1, in FIG. 2.

When the enzyme immobilized membrane of Example 1 was used, a reduction in activity was observed by the first back-washing, but this was the consequence of the flowing out of the non-bonded enzyme by washing. The subsequent reduction in activity was not substantially observed, and this suggests that the enzyme was immobilized stably.

On the other hand, in the case of Comparative Example 1, back-washing caused a greater portion of the enzyme to flow out to bring about a drastic reduction in activity since the polyethyleneimine was not crosslinked.

EXAMPLE 2

A sheet-like polysulfone ultrafiltration membrane ("NTU-3150", made by Nitto Electric Industrial Co., Ltd.) punched into a disc having a diameter of 43 mm, and fixed to a permeation cell for ultrafiltration.

A 0.1 % by weight aqueous solution of polyallylamine (weight average molecular weight 10,000; about 1,750 amino groups per molecule) was passed from the porous layer of the membrane under a pressure of 0.2 kg/cm$^2$ for about 30 minutes.

The porous layer was washed under the same pressure using a large amount of water. A 0.1 % by weight aqueous solution of hexamethylene diisocyanate was then passed under the same pressure as a crosslinking agent to crosslink the polyallylamine held in the porous layer.

The membrane was then sufficiently back-washed with water to remove the polyallylamine not held by the porous layer. A 2.5 % by weight glutaraldehyde solution (phosphate buffer pH 7.0) was passed from the porous layer at room temperature under a pressure of 0.1 kg/cm$^2$ to activate the functional groups of the polyallylamine. The membrane was washed under the same pressure, and a phosphate buffer (pH 7.5) solution of protease ("KOKULASE SS", a product of Sankyo Corporation) having a concentration of 3 mg/ml was passed through the porous layer at 4° C. under a pressure of 0.1 kg/cm$^2$ to immobilize the enzyme by covalent bonds to give an enzyme immobilized membrane.

The resulting enzyme immobilized membrane was sufficiently back-washed with a phosphate buffer (pH 7.5). A 1 % by weight casein solution (phosphate buffer, pH 7.5) was continuously fed into the membrane under a pressure of 0.3 kg/cm$^2$ to perform an enzyme reaction. The protein hydrolysis products in the permeated solution were measured by the Kjeldahl method and precipitation with trichloroacetic acid. It was found that the permeated solution did not form a precipitate with trichloroacetic acid, and a low molecular weight peptide having a concentration of 0.8 by weight (calculated from the amount of nitrogen in the permeated solution) continuously permeated.

While the invention has been described in detail and with reference to specific examples thereof, it will be apparent to one skilled in the art that various changes and modifications can be made therein without departing from the spirit and scope thereof.

What is claimed is:

1. An enzyme immobilized membrane comprising an anisotropic ultrafiltration polysulfone membrane including a dense layer having a molecular cut off from 1,000 to 1,000,000 and a porous layer, the porous layer having retained therein a water-soluble polymer with at least two functional groups in a crosslinked state, and an enzyme being covalently bonded to the functional groups whereby the enzyme is immobilized within the porous layer. wherein said water-soluble polymer is selected from the group consisting of a polyalkyleneimine, a polyaklylene glycol, and a polyallylamine.

2. The enzyme immobilized membrane as in claim 1, wherein the water-soluble polymer is polyethylenemine or polyallylamine.

3. The enzyme immobilized membrane as in claim 1, wherein the water-soluble polymer is cross-linked with a dialdehyde of a dissocyanate.

4. The enzyme immobilized membrane as in claim 1, wherein the enzyme is an enzyme for hydrolyzing polysaccharides or proteins.

5. A process for producing an enzyme immobilized membrane comprising an anisotropic ultrafiltration polysulfone membrane including a dense layer having a molecular cut-off of from 1,000 to 1,000,000 and a porous layer, and enzyme immobilized in the porous layer, which comprises impregnating a solution of a water-soluble polymer having at least two functional groups into the porous layer of said polysulfone membrane under a pressure of from 0.1 to 1.0 Kg/cm$^2$, wherein said water-soluble polymer is selected from the group consisting of a polyalkyleneimine, a polyalkylene glycol, and a polyallylamine, washing the porous layer, passing a solution of a crosslinking agent through the porous layer under a pressure within said pressure range to crosslink the water-soluble polymer.

removing a non-crosslinked portion of the water-soluble polymer by back washing from the dense layer of said polysulfone membrane, and passing a solution of an enzyme under said pressure through the porous layer to covalently bond the enzyme to said functional groups whereby said enzyme is immobilized within the porous layer of said membrane.

6. The process as in claim 5, wherein the water-soluble polymer is polyethyleneimine or polyallylamine.

7. The process as in claim 5, wherein the concentration of the water-soluble polymer solution is 1% by weight or less.

8. The process as in claim 5, wherein, after impregnation, a pressure difference between said porous layer and said dense layer of said ultrafiltration polysulfone membrane is from 0.1 to 0.5 kg/cm$^2$.

9. The process as in claim 5, wherein the crosslinking agent is selected from the group consisting of dialdehydes and diisocyanates.

10. The process as in claim 5, wherein the molar concentration ratio of the functional groups in the water-soluble polymer to the functional groups in the crosslinking agent is from 2 to 50.

11. The process as in claim 5, wherein the enzyme is an enzyme for hydrolyzing polysaccharides or proteins.

* * * * *